United States Patent [19] [11] 4,382,876
Neubold et al. [45] May 10, 1983

[54] METHOD FOR PRODUCING CATALYSTS FOR GAS PHASE OXIDATION OF SATURATED AND/OR UNSATURATED $C_4$-HYDROCARBONS TO MALEIC ANHYDRIDE

[76] Inventors: Kurt Neubold, Lindenstrasse 57m, 4390 Gladbeck; Klaus-Dieter Gollmer, Brahmweg 20, 4250 Bottrop-Kirchhellen, both of Fed. Rep. of Germany

[21] Appl. No.: 244,112

[22] Filed: Mar. 16, 1981

[30] Foreign Application Priority Data

Mar. 20, 1980 [DE] Fed. Rep. of Germany ....... 3010710

[51] Int. Cl.³ ............................................. B01J 27/14
[52] U.S. Cl. ................................................ 252/435
[58] Field of Search ......................................... 252/435

[56] References Cited

U.S. PATENT DOCUMENTS 3,915,892 10/1975 Harrison .......................... 252/437 X
3,985,775 10/1976 Harrison .......................... 252/437 X
4,062,873 12/1977 Harrison .......................... 252/437 X
4,064,070 12/1977 Harrison .............................. 252/435
4,111,963 9/1978 Mount et al. ..................... 252/437 X
4,132,670 1/1979 Katsumoto et al. ................. 252/437
4,147,661 4/1979 Higgins et al. ................... 252/437 X
4,149,992 4/1979 Mount et al. ..................... 252/437 X Primary Examiner—Delbert E. Gantz
Assistant Examiner—William G. Wright
Attorney, Agent, or Firm—Oblon, Fisher, Spivak, McClelland & Maier

[57] ABSTRACT

A method for producing catalysts for gas phase oxidation of saturated or unsaturated hydrocarbons to maleic anhydride is disclosed comprising: (a) mixing a vanadium compound containing pentavalent vanadium with orthophosphoric acid in an alcohol from the series of monohydric lower aliphatic alcohols having 2-8 C-atoms in the optional presence of promoters, and a reducing agent combination of $H_3PO_3$+alcohol wherein the sum of $H_3PO_3$ and $H_3PO_4$ is so controlled that an atomic ratio of P to V of 1.0 to 1.2 is attained and wherein said $H_3PO_3$ is used in such sub-stoichiometric amounts that it is sufficient to reduce the vanadium to an oxidation state only of 4.2 to 4.4, and then said reducing agent combination is used to further reduce the vanadium to an oxidation state between 3.9 to 4.0, any water if present being distilled off as an azeotrope with the alcohol by heating; (b) adding titanium dioxide obtained through high temperature pyrolysis of titanium tetrahalide and optional additional promoters Ni, Fe, Li, Mg; (c) forming precipitated catalyst in a known manner; and (d) activating the catalyst in an oxidation reactor at temperatures of about 450° to 510° C. for about 12 to 72 hours in the presence of an air-hydrocarbon stream.

8 Claims, No Drawings

METHOD FOR PRODUCING CATALYSTS FOR GAS PHASE OXIDATION OF SATURATED AND/OR UNSATURATED C4-HYDROCARBONS TO MALEIC ANHYDRIDE

Economic and ecological considerations have made the replacement of benzene with $C_4$-hydrocarbons as raw materials in the production of maleic anhydride particularly interesting. Consequently, numerous methods of gas phase oxidation from $C_4$-hydrocarbons have been introduced. Depending on the ease with which they can be oxidized, the $C_4$-hydrocarbons are divided into three groups: butadiene, butenes, and butane. These groups generally require different catalysts and reaction conditions in order to carry out the oxidation reaction. Reactivity decreases in the order given above, from butadiene, through the butenes, to butane. Most of the suggested catalysts contain vanadium as one of the components, and after it was discovered that phosphorus greatly increases the selectivity for maleic anhydride production, this element was also included. Normally these components are present as vanadyl phosphate in which vanadium is completely or partially reduced to a lower oxidation state than 5. In most cases the vanadyl phosphate is also promoted with a great variety of materials from the group of alkalis, alkaline earths and the transition elements of the periodic table, to increase the activity and/or the life of the catalysts. The vanadyl phosphate is, however, with some exceptions, the primary component of these catalysts. The V-free catalysts suggested in some cases are usually useful only for the oxidation of butadiene, conceivably also for the butenes, but not for butane.

The activity of vanadyl phosphate catalysts is strongly dependent on the way they are produced. Normally this takes place in aqueous solution in the presence of HCl or oxalic acid as a reducing agent or also with $H_3PO_3$, as Sen Supta, Pat, and Mukherjee (J.C.S., Dalton 1974, 226) have described. These procedures have the disadvantage, however, that large amounts of liquid must be evaporated to dryness in order to obtain the active material, the catalyst raw material, and a certain, usually protracted, drying schedule must be maintained if the pre-catalyst is to develop sufficient activity. For example, rapid drying in a vacuum rotary evaporator or in a spray drier is not possible because the activity is too severely reduced when the water is removed too quickly from the crystalline lattice.

In the search for other procedures it has been suggested to carry out the preparation in organic solvents, usually lower aliphatic alcohols. According to German OS Nos. 27 50 327, 24 27 154, and 23 28 755, isobutanol and HCl gas, and according to German OS No. 27 00 635, and U.S. Pat. Nos. 4,062,873 and 4,064,070 isobutanol and benzyl alcohol, are used as solvents and reducing agents. The disadvantage of these procedures is the need to work with large amounts of gaseous HCl, which are initially introduced into the slurry of $V_2O_5$ in isobutanol, but are liberated again during reflux heating and must be recovered.

Another serious disadvantage is the fact that the catalyst complex goes into solution from which the catalyst raw material can only be recovered by concentrating the solution. It was also determined that with this method the reproducibility of the catalyst activity is not assured. Using benzyl alcohol has the advantage, to be sure, that the catalyst is poorly soluble in the medium, precipitates therefrom and can be recovered by filtration. On the other hand, it has the disadvantage that the rate of reduction is low when alcohols are used, and, as a result, long reflux periods are necessary. Also, water must be azeotropically removed in order to obtain adequate activity. If this is not done, the activity is greatly decreased. The resulting benzaldehyde also causes condensations and blockages when the catalyst is being worked up and prepared for use.

Accordingly, it was the goal of this invention to avoid the disadvantages mentioned above in the production of a vanadyl phosphate catalyst and also to develop a catalyst which gives higher selectivity and yield in the process and can be used in the oxidation of butenes, butadiene, and even butane, or their mixtures. This was achieved through the combination of various measures, as will be described below.

Thus, the object of the invention is a method for producing vanadyl phosphate-based catalysts for gas phase oxidation of saturated and/or unsaturated hydrocarbons to maleic anhydride. The process begins with a vanadium compound containing pentavalent vanadium and orthophosphoric acid using an alcohol chosen from the series of monohydric lower aliphatic alcohols having 2-8 C-atoms as a suspension agent, optionally in the presence of promoters. A combination of $H_3PO_3 +$ alcohol is used as the reducing agent, $H_3PO_3$ being used in such substoichiometric amounts that it is sufficient to reduce the vanadium to an oxidation state of only 4.2 to 4.4, preferably 4.3. Further reduction of the vanadium to an oxidation state between 3.9 and 4.0, preferably 3.95 to 3.98, is produced by the alcohol. The water that may be introduced with the $H_3PO_4$ is distilled off as an azeotrope with the alcohol used. After the vanadyl phosphate is formed, $TiO_2$ prepared by high temperature pyrolysis of titanium tetrahalide is added and optionally the additional promoters Ni, Fe, Li, Mg. The precipitated catalyst is obtained after cooling, filtering, and drying by conventional procedures. The catalyst is activated in the oxidation reactor itself at reaction temperatures of 450° to 510° C. for 12 to 72 hours in the presence of an air-hydrocarbon stream.

It was found that $H_3PO_3$ works as a reducing agent just as well in primary, secondary and tertiary alcohols, preferably with 2-8 C-atoms, as in water. Isobutanol was particularly advantageous. It was surprising that the reaction rate was very high in that case. Since Sen Gupta, Pat, and Mukherjee indicate that the reaction rate in water depends on the acidity of the solution in addition to the temperature, it would not seem obvious that the acidity of $H_3PO_4$ in isobutanol would be adequate to bring about complete reaction of the reducing agent $H_3PO_3$ in a short reaction time. All other possible means of lowering the pH value of the solution, such as adding aqueous HCl, oxalic acid or other organic acids, have proven to be less useful solutions. The $PO_3^{3+}$ ion is oxidized to $PO_4^{3+}$ in this reaction. This is another advantage, because the $PO_4^{3+}$ ion is needed to form vanadyl phosphate in any case, and in this way no foreign material have to be added for the reduction. Another advantage is that the resulting vanadyl phosphate complex is insoluble in the solvent being used and, therefore, can be quantitatively recovered by filtration.

Although known methods such as those described in U.S. Pat. Nos. 3,977,998, 4,092,269 and 4,116,868 and German OS No. 27 27 617, used $H_3PO_3$ in aqueous phase in amounts at least equal to the stoichiometric amount or more (working in part under pressure in an autoclave or with very long reflux times), it was found to be more advantageous with the method according to the invention to use $H_3PO_3$ in an amount smaller than the theoretical value and to leave the rest of the reduction to the desired oxidation state to the isobutanol. It was surprising that the dry precatalyst powder obtained in the production process had a vanadium oxidation state which always stayed in a constant range between 3.90 and 4.0, mostly between 3.95 and 3.98, independent of further processing of the catalyst complex after it is precipitated in isobutanol. The method according to the invention, thus, relates, among other things, to a combined reduction of V with $H_3PO_3$ and alcohols, such as isobutanol.

In accordance with known methods, the pre-catalysts obtained by the process are converted into the active form of the catalyst by calcination at temperatures between 400° and 600° C. in the presence or absence of air. This usually occurs after forming, which is done by conventional procedures by pelletizing, tabletizing or extruding. This process has two main disadvantages:

(1) The apparatus needed for this heating is expensive.

(2) There are problems of oxygen sensitivity of vanadyl(IV) phosphate at high temperatures, making it necessary to exclude $O_2$ or at least considerably reduce the amount of $O_2$ present above about 300° C. Even the often recommended process using a flowing inert gas atmosphere is problematic at 400°–600° C.

In contrast, it was found that it is better for the catalyst raw material produced according to the process of the invention if it is activated in the reactor itself after being formed. Here it is important to operate with as low a temperature as possible, namely a surrounding temperature of 300°–350° C. using a mixture of air with an unsaturated and/or saturated $C_4$-hydrocarbon having a weight ratio of 1:25 to 1:50, preferably 1:30 to 1:40, after preheating to this temperature in an air stream. The hydrocarbon throughput amounts to 10–20 g/cm².hr. Activation takes place as follows: the surrounding temperature is increased so that the reaction temperature (hot spot) reaches 450°–510° C. Activation at this temperature takes 12–72 hours. After this, the "hot spot" is reduced to approximately 480° C. and is further controlled according to the conversion. The final activation of the catalyst is complete after 10–20 days. It should be kept in mind that such a careful and slow formation would hardly be possible outside the reactor. If butane is to be used as the starting material, it is possible to proceed in such a manner that after starting up using, for example, a butene mixture between 300° and 350° C. and increasing the surrounding temperature to 420°–440° C., to switch to butane at this temperature and carry out the further activation exactly as described above. It is also possible to activate a catalyst with butadiene just as well as with butane, butenes or mixtures of the same. It was surprising that the catalysts prepared and activated according to the methods of this invention are equally useful for the selective oxidation of unsaturated as well as saturated $C_4$-hydrocarbons. They can also be used for oxidation of mixtures of unsaturated and saturated $C_4$-hydrocarbons, as occur in the production of the $C_4$-hydrocarbons as, for example, raffinate II of the composition given in Example 1. In the oxidation of such mixtures it should be stressed that, according to the process of the invention, a considerable amount of the butane present is converted along with the butene despite the reaction conditions which depart considerably from those used for oxidation of pure butane. In general, the catalysts for the butene oxidation which work in the known processes leave the butane, more or less of which is present under the appropriate operating conditions, untouched.

Alcohols, for example, isobutanol, have the advantage over water, which can, of course, be used in preparing of catalysts by this process, that the vanadyl(IV) phosphate precipitates almost quantitatively and accordingly is very simply recovered by filtration. When water is used, the product is soluble and can only be recovered by evaporating to dryness. It is also a disadvantage that a definite evaporation schedule must be followed to recover an active catalyst. The catalyst recovered from isobutanol can be dried in any manner, with or without vacuum, without detriment to its activity. In addition, the reproducibility of the catalyst activity for catalysts produced in isobutanol is much better than for those produced in water.

Instead of using the theoretically required amount of $H_3PO_3$ to obtain a vanadium oxidation state 4.0, it is better for the catalyst activity if the amount of $H_3PO_3$ is limited to 60–80% of the theoretical amount. It is particularly advantageous if 70% of the theoretical amount is used. The amount of $H_3PO_3$ in that case is only sufficient to bring the vanadium oxidation state to 4.3. Since the isobutanol itself has reducing properties, the oxidation state of the vanadium is further reduced in the course of the preparation and finally reaches a level in the range of 3.90 to 4.0. Values between 3.95 and 3.98 are attainable in this manner and are very accurately reproducible. Referring to the activation process which is carried out later when the catalyst is activated in the reactor, it is very important that the catalyst powder in the charging operation have a uniform vanadium oxidation state.

Of course, this preparation can be carried out without removing the water, but that has the disadvantage that when a highly dispersed $TiO_2$ is used in the presence of water, a very viscous suspension is produced which, even when thinned, is difficult to filter and produces a catalyst with reduced activity. This disadvantage could be avoided by using 100% $H_3PO_4$, however, this is very difficult to work with because of its physical properties. Therefore, it is preferable to use approximately 85% $H_3PO_4$.

Since the P-compounds are readily soluble in isobutanol, but not the $V_2O_5$, the reaction is heterogenous. Nonetheless, at reflux temperature the reaction rate of the reagents is so great that the total reaction is completed in 4–8 hours. The water introduced with the 85% $H_3PO_4$ is eliminated within the first 60 minutes by distillation. Water and isobutanol form an azeotrope which boils at 90° C. If, within one hour, approximately 15% of the originally used isobutanol is distilled off, the water is removed to a sufficient extent even without an efficient column. The head temperature increases from 90 to approximately 100° C.

$H_3PO_4$ is added so that together with the $H_3PO_3$ a P/V atomic ratio of 1.2 is present. That is a slight excess over the necessary amount, because the final vanadyl(IV) phosphate powder always has a P/V ratio of 1.10. The residual $H_3PO_4$ remains dissolved in the isobutanol mother liquor. It is important to have a slight excess of acid because the reduction of V by $H_3PO_3$ and isobutanol proceeds rapidly enough only in acid solution.

Ti is added in amounts to provide an atomic ratio to V between 0.05 and 0.4. It is added in the form of TiO$_2$, which, for example, is obtained by high temperature pyrolysis of TiCl$_4$. It has greater surface area than normal commercial forms, anatase or rutile (50-80 m$^2$/g as opposed to 5-20 m$^2$/g) and gives the catalyst greater activity than normal anatase, for example.

The promoters Ni, Fe, Li, and Mg are not used in their commercially common salt forms. It has proven to be advantageous, due to the varying solubility of these salts in isobutanol, to produce oxide mixtures which are insoluble or very difficultly soluble in isobutanol by heating salt mixtures at 500°-600° C. These oxide mixtures are added, if desired, together with the highly dispersed TiO$_2$ to the mixture when the water is azeotropically removed. It is advantageous to use compounds such as hydroxides, hydroxide hydrates, hydroxide carbonates or nitrates in this heating. The promotors are used in such amounts that the atomic ratio of Ni or Fe to V is between 0.01 and 0.05 and that of Li or Mg to V is between 0.001 and 0.02. If Ni and Fe are both used, the atomic ratio of the sum to V should lie in the range given above for the individual elements. Either Li or Mg is used, but not both at the same time.

The terms used in the experimental part, such as conversion, yield and selectivity, are defined as follows:

$$\text{Conversion in \%} = \frac{g \, HC \, \text{converted} \cdot 100}{g \, HC \, \text{introduced}} = C$$

$$\text{Yield } MA \text{ in \% by weight} = \frac{g \, MA \cdot 100}{g \, HC \, \text{introduced}} = Y$$

$$\text{Selectivity in mole \%} = \frac{g \, MA \, \text{actual} \cdot 10^4}{g \, MA \, \text{theoretical}} \cdot \frac{C}{100} = S$$

Also the
throughput in g/cm$^2 \cdot$ hr = g HC per cm$^2$ of tube cross-section per hour and the weight ratio =

$$\frac{Air}{HC} \text{ e.g. } 35 = \text{the amount of air in g per g of } HC$$

In the examples the following abbreviations are used:
SBT=salt bath temperature
RT=reaction temperature in the "hot spot" zone
MA=maleic anhydride
HC=hydrocarbon
C=conversion
Y=yield
S=selectivity

EXAMPLES

EXAMPLE 1

A. Catalyst Preparation 1033 g of H$_3$PO$_3$ (enough to achieve a V-oxidation level of 4.3 with quantitative conversion) are stirred and dissolved into 28 l of isobutanol at room temperature. To this are added 3528 g of 85% H$_3$PO$_4$. 3274 g of V$_2$O$_5$ are slurried in this solution, and the slurry is heated to boiling. Approximately 5 l of isobutanol are removed from the reflux during 30-60 min. This distillate contains the free water introduced with the 85% H$_3$PO$_4$. The free water is removed from the mixture in this manner. Then 576 g of TiO$_2$ (surface: 56 m$^2$/g) are added and the suspension is held for 5 hrs. more at reflux.

Then the mixture is cooled to room temperature, the precipitated light blue product is removed by centrifuge and dried for 12 hours at 130° C. in a vacuum of 25-50 mbar. The result is 6.8 kg of grey pre-catalyst with a surface of 31 m$^2$/g and a vanadium oxidation state of 3.98. Its composition is V:P:Ti=1:1.10:0.20.

This pre-catalyst is supplemented with 3% graphite and pressed into tablets with a diameter of 6 mm and a thickness of 4-5 mm. The apparent weight of these tablets is 750-800 g/l.

B. Activating the Catalyst

For this a reactor is used with salt bath cooling and a reactor tube 3.50 m long, having an inner diameter of 25 mm. The reactor tube is provided with a thermal tube with an exterior diameter of 6 mm. The reactor is filled with 1110.17 ml of the above catalyst, corresponding to a fill level of 240 cm. Taking the thermal tube into account, the tube cross-section is 4.6257 cm$^2$.

The catalyst is supplied with an air stream of 500 l/hr and the salt bath is melted and brought to a temperature of 200° C. As more air is passed through, the temperature is raised from 200° to 330° C. in 26 hrs. Beginning at 330° C. a butene-air mixture is passed over the catalyst supplying an amount of butene of 15 g/cm$^2$.hr with an air-butene weight ratio of 35. The commercial butene used had the following composition.

n-butene: 20.19%
iso-butane: 5.81%
butene-1: 46.73%
cis-butene-2: 10.82%
trans-butene-2: 16.20%

The salt bath temperature is then gradually raised from 330° C. approximately 5° C./hr until the reaction temperature in the reaction zone (hot spot) has reached 500° C. (bath temperature approximately 420° C.) and it is held for 12 hrs at this level. During this time the throughput is increased to 20 g/cm$^2$.hr while maintaining the air-butene ratio. The volume space velocity (VSV) now amounts to 2290 hr$^{-1}$. The bath temperature is coordinated with that of the hot spot. After these 12 hrs it is lowered until the conversion is 85-90%. In the next 8-14 days, there is an additional gradual activation during the course of which the bath temperature is lowered further, maintaining constant conversion. Finally, a hot spot temperature of 465° C. is established with a bath temperature of 380° C.

C. Results of Catalyst Testing

The catalyst, produced in accordance with section A and started up and activated according to section B, using the butene described in B as the raw material, yielded the results summarized in Table 1 with a throughput of 20 g/cm$^2$.hr, and an air-butane weight ratio of 35, and a catalyst inlet pressure of 400 mbar:

TABLE 1

| Running Time Days | SBT °C. | RT °C. | C % | Y % by weight | S mole % |
|---|---|---|---|---|---|
| 40 | 380 | 465 | 87.0 | 75.0 | 49.3 |
| 100 | 380 | 465 | 87.0 | 74.0 | 48.7 |
| 200 | 382 | 460 | 86.0 | 71.5 | 47.6 |

EXAMPLE 2

This example describes the introduction of butane (content: 98.7%, 1% isobutane, 0.3% butene) as the raw material to the catalyst produced according to Example 1A.

B. Activating the Catalyst

The catalyst is started up in the same reactor and in the same manner described in Example 1 with the commercial butene having the composition given in Example 1 at 330° C. The salt bath temperature is raised until the hot spot has reached 500° C. While reducing the amount of butene, without changing the amount of air, the salt bath temperature is eventually brought to 430° C. At this temperature the butene is replaced by butane with a resulting throughput of 15 g/cm$^2$.hr. Since the air flow was not changed, the air-butane weight ratio is 35. After the butene is swept out by the butane, the hot spot temperature returns to a value approximately 15°–30° C. above the bath temperature. The bath temperature is raised to 450° C. Thereupon, the hot spot temperature gradually climbs to approximately 500° C. The bath temperature is controlled so that the hot spot temperature stays at this level for 24 hrs. During this time the throughput is raised from 15 to 20 g/cm$^2$.hr while maintaining the air-butane ratio. Then the hot spot temperature is lowered to 480° C. while correspondingly lowering the bath temperature. During the next 8–14 days there is a further gradual activation, during which the hot spot temperature can be lowered further so that the conversion does not exceed 90%.

C. Results of the Catalyst Testing

Using the butane described above as the raw material, an air-butane weight ratio of 35, a catalyst inlet pressure of 400 mbar, and a throughput of 20 g/cm$^2$.hr, the results summarized in Table 2 are obtained:

TABLE 2

| Running time Days | SBT °C. | RT °C. | C % | Y % by weight | S mole % |
|---|---|---|---|---|---|
| 35 | 411 | 455 | 85.0 | 82.5 | 57.5 |
| 80 | 408 | 450 | 84.0 | 80.7 | 56.9 |
| 150 | 410 | 450 | 84.3 | 79.8 | 56.1 |

EXAMPLE 3

A catalyst produced in accordance with Example 1A is poured into a reactor whose reaction tube has a diameter of 22.6 mm and a length of 60 cm. It is provided with a thermal tube having an outer diameter of 6 mm. The volume of the catalyst is 186.4 ml with the fill level at 50 cm. The catalyst, in an air stream, is brought to a salt bath temperature of 350° C. in 4 hours and, at this temperature, a butadiene-air mixture was passed through at a volume space velocity of 1250 hr$^{-1}$ and an air-butadiene weight ratio of 40. Then the salt bath temperature is reduced until the maximum yield is attained. This occurs at 320° C. With quantitative conversion the yield is 112% by weight based on the amount of butadiene used, which corresponds to a selectivity of 61.8 mole %.

EXAMPLE 4

A catalyst is produced according to the method of Example 1A with the exception that, together with the TiO$_2$, a nickel oxide, produced by heating nickel hydroxycarbonate at 500° C., is added in such amount that the atomic ratio of Ni:V=0.02:1. After processing, the catalyst has the following composition: V:P:Ti:Ni=1:1.10:0.20:0.02.

This catalyst is formed into tablets and poured into the reactor described in Example 1B and processed in the following manner:

The reactor is heated to 350° C. while air is passed through. Starting at this temperature, a butane-air mixture is passed over the catalyst in an amount of 15 g/cm$^2$.hr of butane and an air-butane weight ratio of 35. The salt bath temperature is gradually increased at 5° C./hr until the reaction temperature in the hot spot zone has reached approximately 500° C. It is then held at this reaction temperature for 24 hours. The salt bath temperature is then lowered until the reaction temperature reaches 480° C. The temperature remains at this level until the conversion value is between 85 and 90%, which takes several days. Thereafter, the salt bath temperature is regulated so that the conversion is approximately 85%. With a throughput of 20 g of butane/cm$^2$.hr, an air-butane weight ratio of 35 and a catalyst inlet pressure of 400 mbar, the results listed in Table 4 are obtained:

TABLE 4

| Running time Days | SBT °C. | RT °C. | C % | Y % by weight | S mole % |
|---|---|---|---|---|---|
| 28 | 410 | 460 | 87.2 | 84.6 | 57.5 |
| 65 | 406 | 455 | 86.5 | 84.9 | 58.1 |
| 108 | 405 | 455 | 86.1 | 84.1 | 57.8 |

EXAMPLE 5

A catalyst is produced according to the procedure of Example 1A except that together with the TiO$_2$ a mixture of nickel hydroxycarbonate and LiOH.H$_2$O, which has been heated at 500° C., is added in such amount that the atomic ratio of Ni:V=0.03:1 and Li:V=0.01:1. After processing, the catalyst has the following composition: V:P:Ti:Ni:Li:=1.10:0.20:0.03:0.01. This catalyst is made into tablets and poured into the reactor described in Example 1B and processed and activated in accordance with the procedure of Example 2B.

With butane as the raw material, a throughput of 20 g/cm$^2$.hr, an air-butane ratio of 35 and a catalyst inlet pressure of 400 mbar, the results summarized in Table 5 are obtained:

TABLE 5

| Running time Days | SBT °C. | RT °C. | C % | Y % by weight | S mole % |
|---|---|---|---|---|---|
| 30 | 415 | 465 | 82.4 | 80.4 | 57.8 |
| 60 | 412 | 460 | 81.9 | 81.2 | 58.7 |
| 95 | 410 | 455 | 79.6 | 80.7 | 60.1 |

EXAMPLE 6

A catalyst is produced according to the procedure of Example 1A except that together with the TiO$_2$ a mixture of two oxides, produced by heating Fe(NO$_3$)$_2$.9-H$_2$O and magnesium hydroxycarbonate at 500° C., is mixed in such amount that the atomic ratios are Fe:V=0.02:1 and Mg:V=0.005:1. After processing, the catalyst has the following composition: V:P:Ti:Fe:Mg=1:1.10:0.2:0.02:0.005.

This catalyst is made into tablets and poured into reactor described in Example 1B, and processed and activated according to the procedure of Example 2B.

With butane as the raw material, a throughput of 20 g/cm$^2$.hr, an air-butane weight ratio of 35 and a catalyst inlet pressure of 400 mbar, the results shown in Table 6 are obtained:

TABLE 6

| Running time Days | SBT °C. | RT °C. | C % | Y % by weight | S mole % |
|---|---|---|---|---|---|
| 25 | 412 | 470 | 94.3 | 78.4 | 49.3 |
| 50 | 408 | 460 | 91.4 | 81.6 | 52.9 |
| 70 | 406 | 460 | 90.8 | 80.7 | 52.7 |

EXAMPLE 7

A catalyst is produced according to the procedure of Example 1A except that together with the $TiO_2$, an oxide mixture, produced by heating nickel hydroxycarbonate, $Fe(NO_3)_2.9H_2O$ and $LiOH.H_2O$ at 500° C. is added in such an amount that the atomic ratios are Ni:V=0.02:1, Fe:V=0.02:1, and Li:V=0.01. After processing, the catalyst has the following composition: V:P:Ti:Ni:Fe:Li=1:1.10:0.20:0.02:0.02:0.01.

This catalyst is placed as tablets in the reactor of Example 1B and processed and activated according to the procedure of Example 2B.

With butane as the raw material, a throughput of 20 g/cm².hr, an air-butane weight ratio of 35 and a catalyst inlet pressure of 400 mbar, the results shown in Table 7 are obtained:

TABLE 7

| Running time Days | SBT °C. | RT °C. | C % | Y % by weight | S mole % |
|---|---|---|---|---|---|
| 21 | 408 | 465 | 88.4 | 83.9 | 56.3 |
| 48 | 401 | 460 | 87.3 | 83.0 | 56.4 |
| 85 | 398 | 455 | 85.8 | 82.9 | 57.3 |

EXAMPLE 8 (Comparison Example)

This example illustrates the difference between the use of normal $TiO_2$ in the form of anatase and the special, highly dispersed form claimed by us.

A catalyst produced according to Example 1A is poured into a reactor, whose reaction tube has a diameter of 22.6 mm and a length of 60 cm. It is provided with a thermal tube with an outer diameter of 6 mm. The catalyst volume is 186.4 ml with a fill level of 50 cm. The catalyst is brought to 350° C. in an air stream in 4 hrs, and treated with a butane-air stream at 350° C. with a volume space velocity of 1250 hr$^{-1}$ and an air-butane weight ratio of 30. The salt bath temperature is raised from 350° C. in 3 hours until the reaction temperature ("hot spot") reaches 500° C.; after this temperature is held for several hours, the salt bath temperature is reduced until the maximum MA yield is obtained.

The same method is carried out with a catalyst produced according to Example 1A in which the $TiO_2$ with a surface of 56 m²/g is replaced by anatase (0=10.5 m²/g).

Table 8 shows the results obtained with both catalysts:

TABLE 8

| Catalyst | SBT °C. | C % | Amax by weight | S mole % |
|---|---|---|---|---|
| Original | 390 | 88.5 | 88.5 | 59.3 |
| Comparison catalyst with anatase | 390 | 84.0 | 78.5 | 55.4 |

From this it is clear that the maximum yield possible under these conditions when using highly dispersed $TiO_2$ is considerably higher than when using $TiO_2$ in anatase form. Other commercially common forms of $TiO_2$, regardless of whether it is in anatase or rutile form, are clearly inferior to the claimed highly dispersed $TiO_2$.

EXAMPLE 9 (Comparison Example)

In this example, the catalyst produced according to Example 1A is compared with two other catalysts produced according to the same method, but using more reducing agent $H_3PO_3$.

The catalyst according to Example 1A contains enough reducing agent $H_3PO_3$ to produce a vanadium oxidation state $V^x$ of 4.3 by reduction with $H_3PO_3$ alone. Two additional catalysts were produced according to the method of Example 1A in which the amount of $H_3PO_3$ was increased to such an extent (while correspondingly reducing the amount of $H_3PO_4$ so that the P:V ratio remained constant) that a vanadium oxidation state $V^x$ of 4.1 or 4.0 was attained. The three catalysts were tested in the reactor described in comparison Example 8 using the same procedure using butane, and their maximum yields of MA were determined. The results are shown in Table 9:

TABLE 9

| Catalyst | SBT °C. | C % | Amax % by weight | S mole % |
|---|---|---|---|---|
| $V^x = 4.3$ | 390 | 88.5 | 88.5 | 59.3 |
| $V^x = 4.1$ | 440 | 87.3 | 75.1 | 51.0 |
| $V^x = 4.0$ | 440 | 83.6 | 71.9 | 51.0 |

Thus, increasing the amount of the reducing agent $H_3PO_3$ leads to a reduction of catalyst activity; the maximum yield diminishes and is also only achieved at a considerably higher bath temperature.

EXAMPLE 10 (Comparison Example)

In this example, a catalyst (1A) produced according to the procedure of Example 1A is compared with a catalyst during whose production the water was not azeotropically removed (1B).

The two catalysts were tested in the reactor described in comparison Example 8 with the same start-up procedure using a butane-air mixture as in that case, and the maximum yield of MA within the first 4 days was determined. Table 10 shows the results:

TABLE 10

| Catalyst | SBT °C. | C % | Amax % by weight | S mole % |
|---|---|---|---|---|
| 1A | 390 | 88.5 | 88.5 | 59.3 |
| 1B | 400 | 86.3 | 78.9 | 54.2 |

It can be seen that the greater amount of water present in the catalyst 1B during preparation represses the initial activity of the catalyst, as is evidenced by the lower maximum yield and the higher bath temperature at which this is attained.

We claim:

1. A method for producing catalysts for gas phase oxidation of saturated or unsaturated hydrocarbons to maleic anhydride, comprising: (a) mixing a vanadium compound containing pentavalent vanadium with orthophosphoric acid in an alcohol from the series of monohydric lower aliphatic alcohols having 2–8 C-atoms, and a reducing agent combination of $H_3PO_3$+alcohol wherein the sum of $H_3PO_3$ and $H_3PO_4$ is so controlled that an atomic atomic ratio of P to V of 1.0 to 1.2 is attained and wherein said $H_3PO_3$ is used in such substoichiometric amounts that it is sufficient to reduce the vanadium to an oxidation state only of 4.2 to 4.4, and then said reducing agent combination is used to further reduce the vanadium to an oxidation state between 3.9 and 4.0, any water if present being distilled off as an azeotrope with the alcohol by heating; (b) adding titanium dioxide obtained through high temperature pyrolysis of titanium tetrahalide and optional additional promoters Ni, Fe, Li, Mg; (c) forming precipitated catalyst in a known manner; and (d) activating thhe catalyst in an oxidation reactor at temperatures of about 450° to 510° C. for about 12 to 72 hours in the presence of an air-hydrocarbon stream.

2. The method according to claim 1, wherein said titanium dioxide has a surface area of about 50 to 80 $m^2/g$, in an amount to make the atomic ratio of Ti to V between 0.05 and 0.4.

3. The method according to claim 1 wherein nickel and iron, individually or in combination and optionally combined with lithium or magnesium, are used as additional promoters in the form of oxides of these elements obtained through heating salts of these elements at 500°–600° C.

4. The method according to claim 1 or 3 wherein the atomic ratios of Ni or Fe to vanadium or Ni+Fe to vanadium are between 0.01 and 0.05 and those of Li or Mg to vanadium are between 0.001 and 0.02.

5. The method according to claim 1 wherein the catalyst is heated in an air stream to temperatures between 300° and 350° C. before it is activated, and the air in this temperature range is replaced by a mixture of air and an unsaturated or saturated $C_4$-hydrocarbon, and the activation temperature is 450°–510° C.

6. The method according to claim 1 wherein the catalyst is activated at a hydrocarbon throughput of 10–20 g of hydrocarbon/$cm^2$.hr.

7. The method according to claim 1 wherein activation is carried out with an air-hydrocarbon mixture in which the weight ratio of air to hydrocarbon is 25–50:1.

8. A process according to any one of the claims 1–4, 6–7 wherein in step (a) promoters are present.

* * * * *